(12) United States Patent
Edenbaum et al.

(10) Patent No.: US 6,334,855 B2
(45) Date of Patent: Jan. 1, 2002

(54) METHOD FOR MAKING AN ORTHOPEDIC BANDAGE

(75) Inventors: Martin Edenbaum, Princeton Junction, NJ (US); Glenn Jones, Broken Arrow, OK (US)

(73) Assignee: Carapace, Inc., Broken Arrow, OK (US)

( * ) Notice: Subject to any disclaimer, the term of this patent is extended or adjusted under 35 U.S.C. 154(b) by 0 days.

(21) Appl. No.: 09/733,363

(22) Filed: Dec. 8, 2000

Related U.S. Application Data

(62) Division of application No. 09/280,277, filed on Mar. 29, 1999, now Pat. No. 6,206,845.

(51) Int. Cl.⁷ .................................................. A61F 5/00
(52) U.S. Cl. .................................................. 602/6; 602/8
(58) Field of Search ............................................ 602/5–8

(56) References Cited

U.S. PATENT DOCUMENTS

| | | | |
|---|---|---|---|
| 4,100,309 A | 7/1978 | Micklus et al. | 427/2 |
| 4,454,873 A | 6/1984 | Laufenberg et al. | 602/8 |
| 4,667,661 A | 5/1987 | Scholz et al. | 602/8 |
| 4,774,937 A | 10/1988 | Scholz et al. | 602/8 |
| 4,776,331 A | 10/1988 | Simjian | 602/8 |
| 4,856,502 A | 8/1989 | Ersfeld et al. | 602/8 |
| 4,898,159 A | 2/1990 | Buese et al. | 602/8 |
| 4,947,839 A | 8/1990 | Clark et al. | 602/8 |
| 4,960,116 A | 10/1990 | Milner | 602/8 |
| 5,061,555 A | 10/1991 | Edenbaum et al. | 428/253 |
| 5,090,405 A | 2/1992 | Jansen et al. | 602/8 |
| 5,180,632 A | 1/1993 | Edenbaum et al. | 428/253 |
| 5,250,344 A | 10/1993 | Williamson et al. | 428/143 |
| 5,308,642 A | 5/1994 | von Bonin et al. | 427/2 |
| 5,439,439 A | 8/1995 | Green et al. | 602/6 |
| 5,476,440 A | 12/1995 | Edenbaum | 602/8 |
| 5,540,652 A | 7/1996 | Callinan et al. | 602/1 |
| 5,603,691 A | 2/1997 | Scholz et al. | 602/8 |
| 5,713,838 A | 2/1998 | Termanini | 602/8 |
| 5,716,661 A | 2/1998 | Scholz et al. | 427/2.31 |
| 5,738,639 A | 4/1998 | Cueman et al. | 602/6 |
| 5,744,528 A | 4/1998 | Callinan et al. | 524/265 |

FOREIGN PATENT DOCUMENTS

| | | | |
|---|---|---|---|
| EP | 0 266 892 A1 | 5/1988 | A61L/15/07 |
| EP | 0 276 118 A2 | 7/1988 | A61F/13/04 |
| EP | 0 355 635 A1 | 8/1988 | A61L/15/07 |
| EP | 0 295 031 A2 | 12/1988 | C08G/65/32 |
| JP | 02268760 | 2/1990 | A61F/13/04 |

Primary Examiner—Kim M. Lewis
(74) Attorney, Agent, or Firm—Head, Johnson & Kachigian

(57) ABSTRACT

An orthopedic bandage with a curable resin applied to a substrate with the cut ends of the substrate bound together with a binder-detackifier composition. The bandage is constructed by applying stripes of the binder-detackifier agent to the substrate. The substrate is then cut within a stripe of the binder-detackifier composition so that the binding aspect of the composition will stabilize the cut ends of the substrate. A curable resin is also to be applied to the substrate. The detackifying aspect of the composition allows handling of the curable resin while minimizing or eliminating the sticky or tacky feelings normally associated with resins during the curing process. The end placement of the stripes of binder-detackifier allow the user to control the amount of detackifier transferred to the gloves used by the user while applying the bandage both during cast construction and during the final formation.

8 Claims, 2 Drawing Sheets

METHOD FOR MAKING AN ORTHOPEDIC BANDAGE

REFERENCE TO PENDING APPLICATIONS

This application is a divisional of Ser. No. 09/280,277 filed Mar. 29, 1999, now U.S. Pat. No. 6,206,845.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention is directed to an apparatus and method for an orthopedic bandage. More particularly, the invention is directed for use in fiberglass bandages used in making casts and splints when repairing broken bones. The invention has utility and application in areas using resin impregnated substrates and the like.

2. Prior Art

The making of orthopedic bandages is well known. Orthopedic bandage systems are shown in U.S. Pat. No. 4,6,67,661, issued to Scholz et al. on May 26, 1987; U.S. Pat. No. 4,774,937, issued to Scholz et al. on Oct. 4, 1988; U.S. Pat. No. 4,856,502, issued to Ersfeld et al. on Aug. 15, 1989; U.S. Pat. No. 4,898,159, issued to Buese et al on Feb. 6, 1990; U.S. Pat. No. 5,061,555, issued to Edenbaum et al. on Oct. 29, 1991; U.S. Pat. No. 5,250,344, issued to Williamson et al. on Oct. 5, 1993; and U.S. Pat. No. 5,476,440, issued to Edenbaum on Dec. 19, 1995. Each of these patents will be briefly outlined in the following discussion and is hereby incorporated by reference.

U.S. Pat. No. 4,667,661, issued to Scholz et al. on May 26, 1987, discloses a curable resin coated sheet having reduced tack. This invention discloses a sheet material, such as that used for an orthopedic bandage, impregnated with a curable resin and provided with a lubricant at a major surface of the coated sheet. Thus, a layer of lubricating composition is placed in a continuous layer along a major surface of a sheet, or is mixed as an additive to a curable resin and the lubricant resin composition is continuously placed along the major surfaces of a sheet. Similar claims and description of the prior art can be found in the continuation of this patent which resulted in U.S. Pat. No. 4,774,937, issued to Scholz et al. on Oct. 4, 1988 entitled "Curable Resin Coated Sheet Having Reduced Tack". A further description and continuation of the series of patents may be found in U.S. Pat. No. 4,856,502, issued to Ersfeld et al. on Aug. 15, 1989, entitled "Curable Resin Sheets Having Reduced Tack".

U.S. Pat. No. 4,898,159, issued to Buese et al on Feb. 6, 1990 is directed towards the separate art of bindings for bandages and describes ravel-free orthopaedic casting tapes. The description of this invention includes a method of treating substrates to prevent the unraveling and problems associated with untreated fiberglass casting tapes. This invention describes coating the casting tape with a soft, low modulous binder to prevent the casting tape from unraveling when cut. The description includes both continuously coating the entire length of the substrate and applying the binder only at spaced zones where the tape is to be cut.

U.S. Pat. No. 5,061,555, issued to Edenbaum et al. on Oct. 29, 1991, discloses a water-activated orthopedic cast composition having colorant. This patent describes the use of a hydrophilic bisurethane as a detackifying additive. This patent describes adding the detackifier prior to reaction with water, during reaction with water, or after the reaction while the cast is still wet. Specifically, this patent addresses using a drum roller or paddle mixer to obtain an even distribution of the detackifying material throughout the prepolymer.

U.S. Pat. No. 5,250,344, issued to Williamson et al. on Oct. 5, 1993, discloses a cast material with encapsulated lubricant. This invention describes an orthopedic cast which uses a resin material embedded into a planar substrate which has been coated by an encapsulated lubricous material. The encapsulated lubricous material has been encapsulated into a plurality of microgranuals wherein the microgranuals are deposited only onto one end portion of the tape, such that the microgranual encapsulated lubricant is only on the innermost end of a roll of cast forming tape.

U.S. Pat. No. 5,476,440, issued to Edenbaum on Dec. 19, 1995, discloses an orthopedic bandage with lubricous core. This patent teaches the bandage with a core containing lubricant material which renders the surface portion of the bandage substantially non-tacky to facilitate the forming of a cast. The cores are designed to have a liquid-permeable base which releases lubricating liquid upon application of a force to the core. In this manner the lubricant will be dispensed onto the appliers gloves to allow for the forming of the cast.

European Patent Application No. 0295031 describes surfactants that can be incorporated throughout the resin by dissolution into the resin prior to spreading the resin onto the substrate. This European patent application and the associated disclosures is hereby incorporated by reference.

The above described bandages suffer from the drawbacks of wasting material by coating the entire bandage with lubricant, only coating the inner end of the bandage with lubricant, failing to combine binding agents and lubricants, and using expensive methods VD such as microencapsulation to distribute the lubricant for its use. Furthermore, the systems disclosed in the patents do not appear to allow the technician to adjust the amount of lubrication both during and after the cast application.

Hence, there is a need for an eloquently simple orthopedic bandage with a combined end binding agent and lubrication system.

SUMMARY OF THE INVENTION

In accordance with the present invention, an improved orthopedic bandage and method for constructing an orthopedic bandage are provided. The invention comprises an orthopedic bandage with a curable resin applied to a substrate with the ends of the substrate bound together with a binder-detackifier composition. In a preferred embodiment, the bandage is constructed by applying stripes of binder-detackifier agent to the substrate. The substrate is then cut within a stripe of the binder-detackifier composition so that the binding aspect of the composition will stabilize the ends of the substrate. A curable resin is also to be applied to the substrate. The detackifying aspect of the composition allows handling of the curable resin while minimizing or eliminating the sticky or tacky feelings normally associated with resins during the curing process. The end placement of the stripes of binder-detackifier allows the user to control the amount of detackifier transferred to the gloves of the user both during cast construction and during the final formation.

Other objects and further scope of the applicability of the present invention will become apparent in the detailed description and examples to follow, taken in conjunction with the accompanying drawings wherein like parts are designated by like reference numerals.

DETAILED DESCRIPTION OF THE PREFERRED EMBODIMENTS

Figure 1:
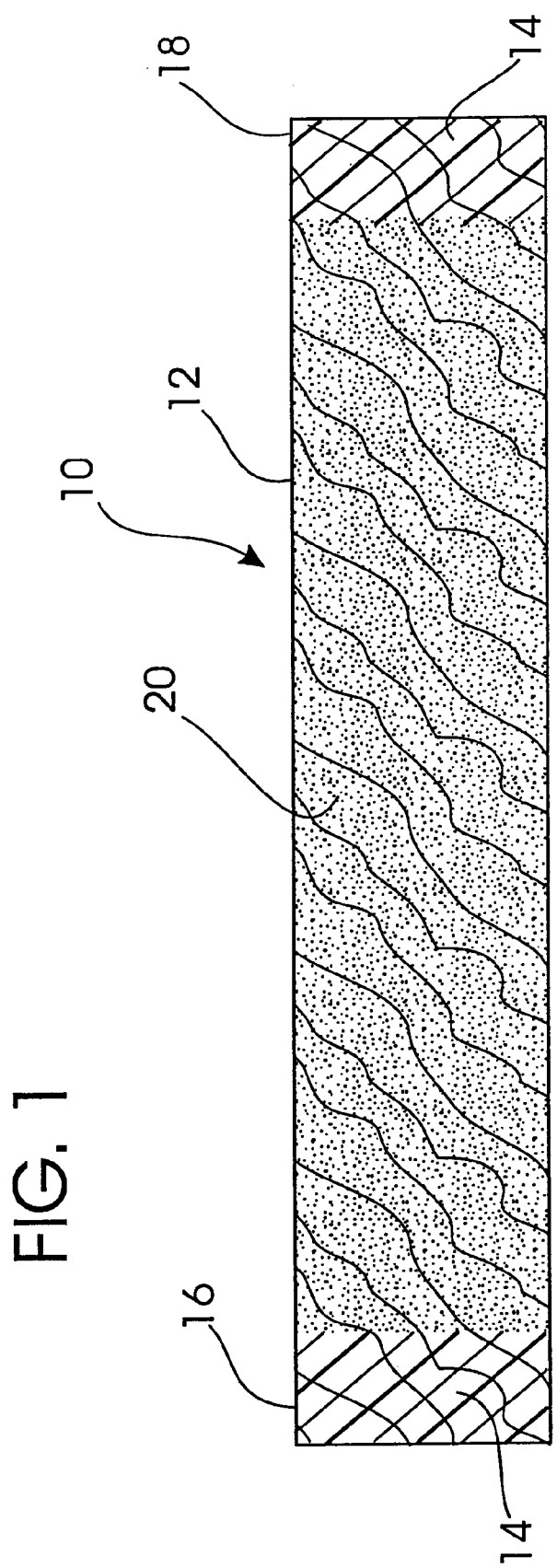
FIG. 1 is a schematic representation of a discrete orthopedic bandage segment of the present invention.
Figure 2:
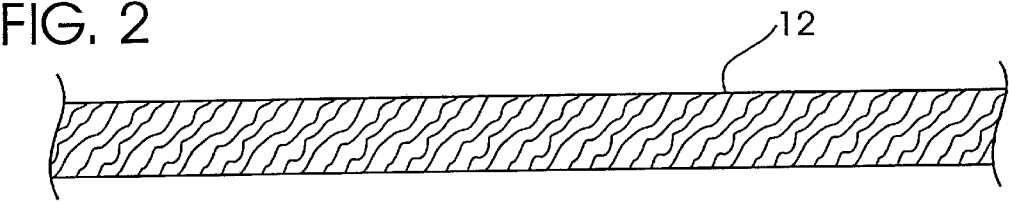
FIG. 2 is a schematic representation of an elongated substrate.

As shown in FIGS. 1–6 of the drawings, an improved orthopedic bandage and method for constructing a discrete orthopedic bandage segment 10 are provided. The invention comprises an orthopedic bandage 10 with a curable resin 20 applied to a substrate 12 with the ends 16 and 18 of the substrate 12 bound together with a binder-detackifier composition 14. The bandage 10 is constructed by applying stripes of the binder-detackifier 14 to the substrate 12. The substrate 12 is then cut within a stripe of the binder-detackifier composition 14 so that the binding aspect of the composition will stabilize the ends 16 and 18 of the substrate 12. A curable resin 20 is applied to the substrate 12 either before or after application of the binder-detackifier stripes. The detackifying aspect of the binder-detackifier composition 14 allows handling of the curable resin 20 while minimizing or eliminating the sticky or tacky feelings normally associated with resins 20 during the curing process. The end placement of the stripes of binder-detackifier 14 allow the user to control the amount of detackifier transferred to the user's gloves both during cast construction and during the final formation.

As shown in FIGS. 1–6 of the drawings, the preferred embodiment of the orthopedic bandage 10 of this invention uses a substrate material 12 which may be coated with a binder-detackifier 14 and may be impregnated with a resin 20. The substrate 12 can be formed from a single type of fiber, or a combination of fibers as well known in the prior art. Generally, an orthopedic bandage substrate 12 is constructed from glass fiber, cotton, flax, rayon, rayon, wool, acrylic, resin, nylon, polyester, or the like. This provides a strong, yet flexible substrate 12 for the bandage 10.

An additional item used in the construction of the preferred embodiment of this invention is the binder-detackifier 14. This binder-detackifier 14 is constructed from a polybithane, hydrophilics, surfacants, polysiloxane, or similar detackifiers and the like and is designed to form a waxy, water-sensitive solid at room temperatures. The preferred embodiment uses a water soluble base for the poly-bithane and is designed to melt to a viscous liquid at slightly elevated temperatures. Generally, a melting point of approximately 250 degrees Fahrenheit is used to allow for easy application of the binder-detackifier 14 during the method for constructing the bandage 10, while ensuring that the binder-detackifier 14 remains a solid at room temperatures. This allows for the binder-detackifier 14 to be applied to the bandage 10 as a hot liquid band in order to properly coat the substrate 12. This allows the liquid binder-detackifier 14 to penetrate the substrate 12 and properly bond the fibers in the substrate 12 together. By coating the substrate 12 in this manner, the binder-detackifier 14 will prevent the unraveling of the substrate 12 fibers when the substrate 12 is cut. This allows the formation of a safe and attractive cut across the substrate 12 for the first end 16 and second end 18 of a discrete bandage segment 10. Additionally, this coating process allows the binder-detackifier 14 to fully coat both sides of the bandage 10 to allow for contact with the binder-detackifier 14 on either side of the bandage 10. This multiple side access allows the bandage 10 to be rolled and used in any manner without regard for the location of the binder-detackifier 14.

The binder-detackifier 14 will generally be applied at the first end 16 and second end 18 portions of a bandage 10 to allow the user to control the amount of contact he or she has with the binder-detackifier agent. Note that the preferred embodiment also allows for the binder-detackifier 14 to become activated in water for transferring the detackifier properties to the gloves of the user of the bandage 10.

If the user desires to eliminate the detackifying properties during the formation of the bandage 10, the user may simply change gloves during the process. Because the preferred embodiment only uses the binder-detackifier 14 at the ends 16 and 18 of the bandage 10, the users gloves will contact binder-detackifier 14 at the first end 16 of the cast construction process and will not contact additional binder-detackifier 14 until the second end 18 of the bandage 10 is exposed during the cast construction process. This allows the user to control the amount of binder-detackifier 14 used during the construction of the cast. Another method for controlling the amount of detackifier used during the construction of the cast is to limit or increase the amount of contact the user has with the initial stripe of binder-detackifier 14. By reducing the amount of contact with the binder-detackifier 14, the user will increase the tackiness feel of the bandage's resin 20. Alternatively, the user may increase the amount of contact with the initial stripe of binder-detackifier 14 to increase the slipperiness feeling of the resin 20, and thus reduce the tackiness feel of the resin 20. This allows the user to control the tackiness level of the bandage 10 during the construction of the cast. This same process may also be used to control the amount of binder-detackifier 14 that is used during the final smoothing of the cast by increasing or decreasing the contact with the final end of the bandage 10. Thus, the detackifier should work with a compatible resin 20.

As well described in the prior art, resins 20 are generally constructed from water curable pre-polymers or similar materials. Known resins include plaster of paris, vinyl monomers, polyurethanes, cyanoacrylate esters, polyisocyante prepolymer and propylene glycol, and the like. Note that the binder-detackifier and resin must be chosen for compatibility.

Figure 3:
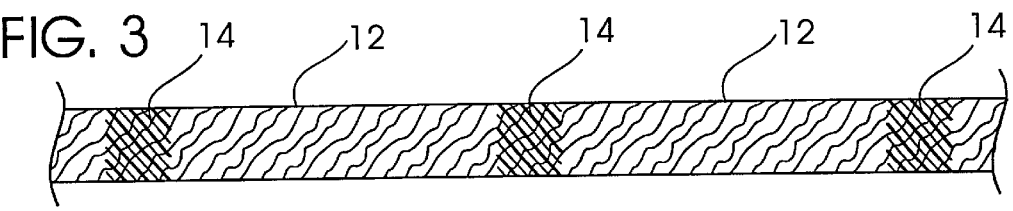
FIG. 3 is a schematic representation of an elongated substrate coated with stripes of a binder-detackifier.
Figure 4:
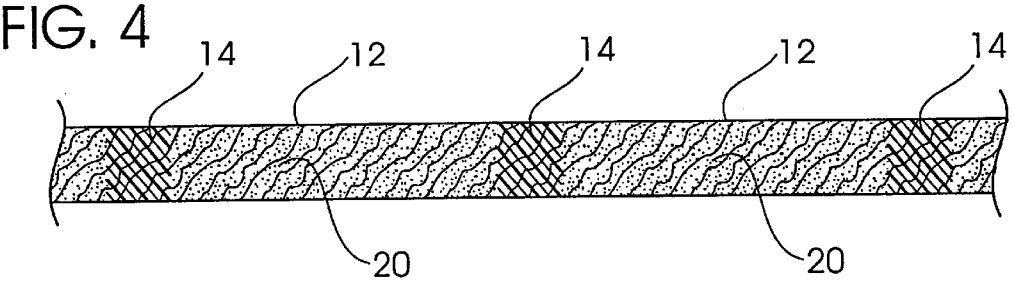
FIG. 4 is a schematic representation of an elongated substrate coated with stripes of a binder-detackifier and also impregnated with a resin.
Figure 5:
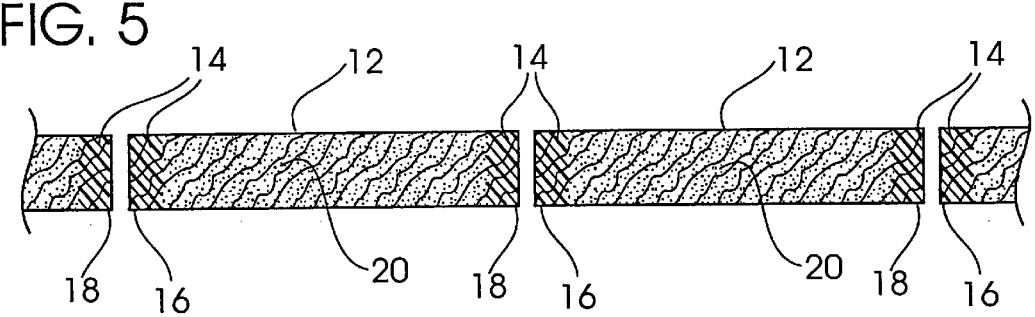
FIG. 5 is a schematic representation of an elongated substrate coated with stripes of a binder-detackifier and impregnated with a resin which is cut into discrete segments.

As shown in FIGS. 2–6, the preferred embodiment of the present invention makes an orthopedic bandage 10 by coating a substrate 12 with a binder-detackifier composition 14, and cutting the substrate 12 at a location that is coated with the binder-detackifier composition 14 to form the discrete bandage 10 segments. As shown in FIG. 4, the substrate 12 may be impregnated with a resin 20 before the cutting of the substrate 12. However, it is also anticipated that the resin 20 may be impregnated into the substrate 12 after the substrate 12 is cut into discrete segments 10. While the preferred embodiment only impregnates the substrate 12 with the resin 20 along the central portion of the bandage 10, it is possible for the resin 20 to be continuous along the length of said substrate 12. As shown in FIGS. 3 and 4, the preferred embodiment only has binder-detackifier 14 coated at intervals where the substrate 12 will be cut so that the binder-detackifier 14 will be positioned at the ends 16 and 18 of the discrete bandage sections 10. While the preferred embodiment coats substrate 12 with binder-detackifier 14 prior to impregnating substrate 12 with resin 20, it is possible for resin 20 to be impregnated into substrate 12 prior to coating substrate 12 with binder-detackifier 14.

While the preferred embodiment coats substrate 12 with binder-detackifier 14 in a stripe pattern, it is possible to coat substrate 12 with binder-detackifier 14 in multiple different patterns, such as swirls or cross-hatch.

By constructing the bandage 10 according to this method, an orthopedic bandage 10 is formed from a substrate 12 which has been impregnated by a resin 20 and has been coated with binder-detackifier 14. This construction allows for the binder-detackifier 14 to use its binder properties to control the unraveling of the fibers of said substrate 12. In addition, the placement of the binder-detackifier 14 allows a user of the bandage 10 to control the tackiness of the resin 20 by controlling the amount of contact with the binder-detackifier composition 14. By controlling the amount of contact with the binder-detackifier 14, the user can control the amount of the binder-detackifier 14 which is used and thus, the user can control the detackifier properties associated with the construction and formation of the cast being made from the orthopedic bandage 10.

As shown in FIG. 1, one method for controlling the detackifying properties of the binder-detackifier 14 is to place stripes of binder-detackifier 14 only on the ends 16 and 18 of the bandage 10. This allows the binding properties of the binder-detackifier 14 to work against the unraveling of the fibers of the bandage 10 when it is cut, but still allows the user to control the amount of detackifier initially used during the formation of the bandage 10. The second end then allows the user access to additional binder-detackifier 14 at the end of the cast construction process so that more of the binder-detackifier 14 and its detackifier properties can be used during the final formation of the cast. This allows the user to control the tackiness of the resin 20 during the wrapping of the orthopedic bandage 10 and also allows the user access to additional detackifier during the final smoothing operation of the cast construction.

Figure 6:
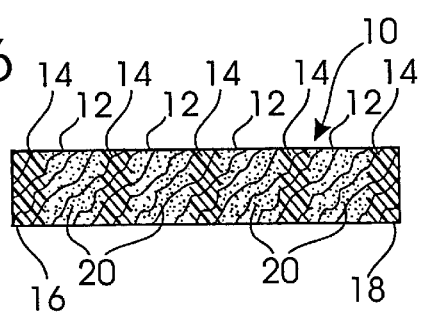
FIG. 6 is a schematic representation of a discrete orthopedic bandage segment with alternating stripes of binder-detackifier and continuously impregnated with resin.

As shown in FIG. 6 of the drawings, Another embodiment of the method of the present invention would have stripes of binder-detackifier 14 placed at intervals along the bandage 10. This will allow the user to have access to additional binder-detackifier 14 without the constant contact that a continuous impregnation of the substrate 12 would have, thus permitting the user to adjust the amount of binder-detackifier 14 either up or down, depending on the requirements of the application or process.

EXAMPLE I

This example is included to serve as a control to calibrate the testing apparatus and methodology utilized to determine the kinetic coefficient of friction (KCOF) of the examples set out below.

The test apparatus used was the Instron Model 2810-005 COF fixture modified as described in U.S. Pat. No. 4,774,937 which discloses low coefficient of friction orthopedic casting materials The KCOF testing procedure utilized an Instron 4505 Universal Testing Machine with Series IX software to conduct, record and analyze the test data.

The test material for Example I was a production sample sold under the name of Scotchcast Plus by the 3M Company. The average KCOF of this product was found to be 0.3 and the material was reported to feel very slippery during application and molding.

EXAMPLE II

The KCOF testing procedure and apparatus in Example I was repeated using a product sold under the name CaraGlas™ by Carapace®. This product contains no detackifying modifier. The average KCOF of this product was found to be 2.2. The material was reported by feel very tacky during application and was difficult to mold because of the tackiness.

EXAMPLE III

The test material for Example III was prepared by applying 0.45 grams of Polybithane, as described in U.S. Pat. No. 5,061,555, in a ⅜ inch wide band on both ends of a 3 inch by 4 yard bandage of the product in Example II, CaraGlas™ by Carapace®, and preparing the sample for the KCOF test apparatus as follows:

1) Immerse the bandage in water with one hand and pump it for about 15 seconds.
2) Remove the bandage and squeeze and twist lightly for about 5 seconds to distribute the Polybithane over both gloves.
3) Cut the bandage to the length needed for testing (24 inches).
4) Place the end band coated end into the test holder.
5) Wipe the exposed surface of the bandage once with the gloved hand which held the bandage during pumping.
6) Place the sled on the sample and complete the test.

The KCOF testing procedure and apparatus in Example I was repeated using a sample of this test material. The average KCOF of this sample was found to be 1.7. The maximum KCOF claimed in the '937 patent is 1.2, above which the material feels tacky. It was also reported that by simple manipulation of the beginning and end bands of Polybithane, the bandage could be applied and molded without the tacky feel as reported in Example II and that the level of nontackiness could be easily and readily adjusted.

EXAMPLE IV

The test material for Example IV was prepared by adding 1.5% Polybithane to the resin used in the product CaraGlas™ by Carapace® and coating this modified resin on the standard knitted fiberglass backing at standard coating weight (41% resin by weight).

The KCOF testing procedure and apparatus in Example I was repeated using a sample of this test material. The average KCOF of this material was found to be 1.7. It was also reported that the test material felt tacky during application and was difficult to mold because it was tacky.

The Polybithane concentration selected for this example is the same as that of Example III, but instead of being concentrated in the end bands as it is in Example III, the Polybithane is evenly distributed throughout the resin. This demonstrates the uniqueness of the end band concept as disclosed by the present invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method for making an orthopedic bandage comprising:
    coating a substrate with a continuous binder detackifier composition along the length of said substrate; and
    impregnating said substrate with a resin at intervals along said substrate.

2. The method for making an orthopedic bandage of claim 1, further comprising:
    cutting said substrate at a location coated with said binder-detackifier composition to form discrete bandage segments.

3. A method for making an orthopedic bandage comprising:
    coating a substrate with a binder detackifier composition at intervals along the length of said substrate; and
    impregnating said substrate with a resin at intervals along said substrate.

4. The method for making an orthopedic bandage of claim 3, further comprising:
    cutting said substrate at a location coated with said binder-detackifier composition to form discrete bandage segments.

5. A method for making an orthopedic bandage comprising:
    impregnating a substrate with a continuous resin composition along the length of said substrate; and
    coating said substrate with a continuous binder detackifier composition along the length of said substrate.

6. The method for making an orthopedic bandage of claim 5, further comprising:
    cutting said substrate to form discrete bandage segments.

7. A method for making an orthopedic bandage comprising:
    impregnating a substrate with a continuous resin composition along the length of said substrate; and
    coating said substrate with a binder detackifier composition at intervals along the length of said substrate.

8. The method for making an orthopedic bandage of claim 7, further comprising:
    cutting said substrate to form discrete bandage segments.

* * * * *